US005788962A

United States Patent [19]

Wise et al.

[11] Patent Number: 5,788,962

[45] Date of Patent: Aug. 4, 1998

[54] **DNA SEQUENCES CODING FOR *MYCOPLASMA HYOPNEUMONIAE* SURFACE ANTIGENS, CORRESPONDING PROTEINS AND USE IN VACCINES AND DIAGNOSTIC PROCEDURES**

[75] Inventors: Kim S. Wise; Mark A. McIntosh, both of Columbia, Mo.

[73] Assignee: The Curators of the University of Missouri, Columbia, Mo.

[21] Appl. No.: 703,947

[22] Filed: Aug. 28, 1996

Related U.S. Application Data

[63] Continuation of Ser. No. 373,957, Jan. 17, 1995, abandoned.

[51] Int. Cl.$^6$ .......... A61K 39/02

[52] U.S. Cl. .......... 424/264.1; 424/234.1; 435/69.3; 435/69.7; 530/350; 536/23.7

[58] Field of Search .......... 435/69.3, 69.7; 424/264.1, 234.1; 530/350; 536/23.7

[56] References Cited

U.S. PATENT DOCUMENTS 5,240,706 8/1993 Faulds .......... 424/92

FOREIGN PATENT DOCUMENTS 9118627 12/1991 WIPO .
92033157 3/1993 WIPO .

OTHER PUBLICATIONS

Wise et al. J. Bacteriol. 1987. 169(12):5546–5555.

Kim et al. Infect. Immun. 1990. 58(8):2637–3643.

*Primary Examiner*—James C. Housel
*Assistant Examiner*—Jennifer Shaver
*Attorney, Agent, or Firm*—Grace J. Fishel

[57] ABSTRACT

*Mycoplasma hyopneumoniae* P65 surface antigens prepared by recombinant DNA or synthetic methods, protein antigens encoded by P65 gene, an expression vector and transformed host containing the antigens, a vaccine based on such antigens, methods of treating swine, etc. to prevent enzootic pneumonia using that vaccine and diagnostic tests to detect the presence of *Mycoplasma hyopneumoniae*.

3 Claims, 17 Drawing Sheets

Fig. 1A

```
AAGCTTGAGA AAATTACAAA AAAATTCATT TTCCAAAAAC GCTTTTAGCT             50

TTTATTAAAG GGCCCAAAGT TTTTAATGAA GTTCAAAATT GTAAAAATTG            100

TAATTATAAA ATCATTAAAG TTAATAATAA TATAAATAAA AAAATTTTTA            150

TCGCATTTAA ACAAGTTTCT TAATAATTTT GAATTTTAAT TTAGAAAATA            200

TAAAAATCTT GTTGATTTTT ATATAATTTT TTAACCTTTT TTTTTTTTTT            250

TTTTTTTTTA GGAATATGGT AAAATTTAGT CCATCTATCA AAAATATAGA            300

AAAGGAAAAA TT   ATG AAG AAA AAA GCA AGA AAA TTC TTA AGA CTA       345
                Met Lys Lys Lys Ala Arg Lys Phe Leu Arg Leu
                1               5                   10

ACT TCG CTT ACA CTA GCG CCT TTT TCG GTC TTC ACC ACT CTT ATT       390
Thr Ser Leu Thr Leu Ala Pro Phe Ser Val Phe Thr Thr Leu Ile
            15                  20                  25

TCA GCT GGT TGT TTG CAA AAA AAT TCT TTG CTT TCA GAA GTA AAT       435
Ser Ala Gly Cys Leu Gln Lys Asn Ser Leu Leu Ser Glu Val Asn
            30                  35                  40

TAT TTA GCC CTA GGT GAT TCA CTA ACA GCT GGA TTT AAT GAA GAA       480
Tyr Leu Ala Leu Gly Asp Ser Leu Thr Ala Gly Phe Asn Glu Glu
            45                  50                  55
```

MATCH WITH Fig. 1B

MATCH WITH Fig. 1A

Fig. 1B

```
ACA TAC CGT GAT TTT CAA GGT ACT TTA GAT AAA GAT GGT AAT TTA AGC    528
Thr Tyr Arg Asp Phe Gln Gly Thr Leu Asp Lys Asp Gly Asn Leu Ser
             60                  65                  70

GGT CAA TCT TAT CCT GCT TAT TTT GCT TAT TAT CTA CAA AAA CTT AAT    576
Gly Gln Ser Tyr Pro Ala Tyr Phe Ala Tyr Tyr Leu Gln Lys Leu Asn
         75                  80                  85

AAG AAT TCA CTT GTT TCT TAT GAT AAT TTG GCA ATT TCT GGG ACA ACA    624
Lys Asn Ser Leu Val Ser Tyr Asp Asn Leu Ala Ile Ser Gly Thr Thr
     90                  95                 100

ACA GAA AAC TGA CTT TAC CTT CTT AAT CCA ACC AAA TAT CCA AAT GGA    672
Thr Glu Asn Trp Leu Tyr Leu Leu Asn Pro Thr Lys Tyr Pro Asn Gly
105                 110                 115                 120

AAA ATG AGC GAT AAT CCG TTA GTT ACA AAC TAT TCA GGA AAT GAA AAA    720
Lys Met Ser Asp Asn Pro Leu Val Thr Asn Tyr Ser Gly Asn Glu Lys
                125                 130                 135

TAT AAT GAA ATA GGC TCT GTT TTT GGT GAT TTT AAT AAG GAT TCC TAT    768
Tyr Asn Glu Ile Gly Ser Val Phe Gly Asp Phe Asn Lys Asp Ser Tyr
            140                 145                 150

CCT GGT TTA GTC GAA AAA GTT AAA AAA GCA AAC CTT TTG ACA ATG TCA    816
Pro Gly Leu Val Glu Lys Val Lys Lys Ala Asn Leu Leu Thr Met Ser
        155                 160                 165
```

MATCH WITH Fig. 1C

Fig. 1C

MATCH WITH Fig. 1B

```
GTG GGA GCT AAC GAT CCT TTT TTA GCA ATT TTT AAT GAA TTT AAA AAA    864
Val Gly Ala Asn Asp Pro Phe Leu Ala Ile Phe Asn Glu Phe Lys Lys
    170                 175                 180

TGA GCA AGT ATA ATA AAA CCA AAA TCA GAG GAA GCA AAA AAA TTA CTA    912
Trp Ala Ser Ile Ile Lys Pro Lys Ser Glu Glu Ala Lys Lys Leu Leu
185                 190                 195                 200

GAT CCA AAT GAA AGA GCG AAT TTC CTA GCA GAA AAA GGA ATG CTT TTA    960
Asp Pro Asn Glu Arg Ala Asn Phe Leu Ala Glu Lys Gly Met Leu Leu
                205                 210                 215

AAG GCG GAA GTT AAT AAA AAA ATT GAG GAA ATA AAC ACA AAT CTT GAT   1008
Lys Ala Glu Val Asn Lys Lys Ile Glu Glu Ile Asn Thr Asn Leu Asp
            220                 225                 230

AAT TTA ATT AAA GAA TTA AAG GCG CTT AAT CCA AAA TTA AGT ATA AAT   1056
Asn Leu Ile Lys Glu Leu Lys Ala Leu Asn Pro Lys Leu Ser Ile Asn
        235                 240                 245

TTA GTT GGA TAT AAA TTG CCA AAT TCC GGT TTT ATT AAG ATT TTA AAG   1104
Leu Val Gly Tyr Lys Leu Pro Asn Ser Gly Phe Ile Lys Ile Leu Lys
    250                 255                 260

TAT CTT TTA TAT ACT TAT GCA AAA ATT GAA ACG GAC TTT ATC AAT GAA   1152
Tyr Leu Leu Tyr Thr Tyr Ala Lys Ile Glu Thr Asp Phe Ile Asn Glu
265                 270                 275                 280
```

MATCH WITH Fig. 1D

MATCH WITH Fig. 1C

Fig. 1D

```
ATT CCC GAA AAA ATT AAC AAA ATT ATT CGT GAA ACC GCC ATT AAA AAT      1200
Ile Pro Glu Lys Ile Asn Lys Ile Ile Arg Glu Thr Ala Ile Lys Asn
                285                 290                 295

AAG GTA AAT TAT ATT GAT GTC TAT GAT AAA AGT ATT TGA AAT GAT TCT      1248
Lys Val Asn Tyr Ile Asp Val Tyr Asp Lys Ser Ile Trp Asn Asp Ser
            300                 305                 310

GAT AAA AAT TTA ATG GCG AAA AAT TTT GAC TTC CAC CCT TCA ATT CAA      1296
Asp Lys Asn Leu Met Ala Lys Asn Phe Asp Phe His Pro Ser Ile Gln
        315                 320                 325

GGT TAT AAA AAA ATT GCT CAC CAA CTT TTG TTA AAA TTA ACT CTT GAC      1344
Gly Tyr Lys Lys Ile Ala His Gln Leu Leu Leu Lys Leu Thr Leu Asp
    330                 335                 340

CAA GAA GAA AAA GAT GAT TCT AAT GCT GAA GAG CTA AAA AAT ACT ACA      1392
Gln Glu Glu Lys Asp Asp Ser Asn Ala Glu Glu Leu Lys Asn Thr Thr
345                 350                 355                 360

AAT TTC GAT GAT TTT GAT GAG AAT AAA CCG ACC TAT TCC AAA GTT ATT      1440
Asn Phe Asp Asp Phe Asp Glu Asn Lys Pro Thr Tyr Ser Lys Val Ile
                365                 370                 375

GAC CTA AGT GTT TTT GCA AAA TCA AAT AAA GAA TTT CTT GAA AAA TTA      1488
Asp Leu Ser Val Phe Ala Lys Ser Asn Lys Glu Phe Leu Glu Lys Leu
            380                 385                 390
```

MATCH WITH Fig. 1E

Fig. 1E

MATCH WITH Fig. 1D

```
AAC GAA AAT AAG CAA ACT AGT GAA TTT ATT GCT CAA AAA TCC ACT TTT     1536
Asn Glu Asn Lys Gln Thr Ser Glu Phe Ile Ala Gln Lys Ser Thr Phe
        395                 400                 405

GAC ACC GAT CAA GAA GCT GCA ATC AAA GAC GAC AAA CGC ACT TTT         1581
Asp Thr Asp Gln Glu Ala Ala Ile Lys Asp Asp Lys Arg Thr Phe
    410                 415                 420

GGA AAT ATA GTT CGA GAA ATT GTA TCT TTA CCA ATC TTC GAT AAT         1626
Gly Asn Ile Val Arg Glu Ile Val Ser Leu Pro Ile Phe Asp Asn
    425                 430                 435

TTT GAT TTT AGA GAG TTA ATA CCT GTT AAA AAT CCA TTT GTA AAA         1671
Phe Asp Phe Arg Glu Leu Ile Pro Val Lys Asn Pro Phe Val Lys
    440                 445                 450

GCA ATT ATT AAC AGC TAT TTA GGG AAA CCA GCT GGT TCT CTT ATA         1716
Ala Ile Ile Asn Ser Tyr Leu Gly Lys Pro Ala Gly Ser Leu Ile
    455                 460                 465

AAA GAT ATC GAA CAA CTC GAA AAT AAA GTG AAA GAT TAC GCA AGA         1761
Lys Asp Ile Glu Gln Leu Glu Asn Lys Val Lys Asp Tyr Ala Arg
    470                 475                 480

CCT AAT ATC AAG ATT TTC GAT ACA ATT ATT GAC TCA TTC ATA AGA         1806
Pro Asn Ile Lys Ile Phe Asp Thr Ile Ile Asp Ser Phe Ile Arg
    485                 490                 495
```

MATCH WITH Fig. 1F

Fig. 1F

MATCH WITH Fig. 1E

```
AAA ATG GTA GCA TTT TTT GCT GAA TTA AAC ACT GAT CAA GAA ATA     1851
Lys Met Val Ala Phe Phe Ala Glu Leu Asn Thr Asp Gln Glu Ile
    500                 505                 510

AAA GAA TTC AAA ATG TCA CCT CAA ATA CTA TTT CTG ACA CTA AGA     1896
Lys Glu Phe Lys Met Ser Pro Gln Ile Leu Phe Leu Thr Leu Arg
    515                 520                 525

AAT GCA ATA CTA AGT CCA TTT GAT TTA ACT AAA TTA AAA GAC AGT     1941
Asn Ala Ile Leu Ser Pro Phe Asp Leu Thr Lys Leu Lys Asp Ser
    530                 535                 540

GCT ACA TTT AAA ATT TTA ATG AAT CTC AAA CCA GAA CAA ATA TTA     1986
Ala Thr Phe Lys Ile Leu Met Asn Leu Lys Pro Glu Gln Ile Leu
    545                 550                 555

ACT CTA CTA GGC CTA GGT AAA ACC CCT TCA GTT CCT AAA CCT GAA     2031
Thr Leu Leu Gly Leu Gly Lys Thr Pro Ser Val Pro Lys Pro Glu
    560                 565                 570

AAA CCA AAA GAT CAA GGT TCT ATG CCA CAA ACA GAT ACT TCT AGT     2076
Lys Pro Lys Asp Gln Gly Ser Met Pro Gln Thr Asp Thr Ser Ser
    575                 580                 585

CAA AAA CAA GAA AGC GGA ACA GGT TCA ACA GAT TCA ACA AAA GCT     2121
Gln Lys Gln Glu Ser Gly Thr Gly Ser Thr Asp Ser Thr Lys Ala
    590                 595                 600
```

MATCH WITH Fig. 1G

MATCH WITH Fig. 1F

Fig. 1G

```
ACA ACT GAA AAC CAA AAA CCA GCT GAG CAA ACA AAT TCT TCT GAG       2166
Thr Thr Glu Asn Gln Lys Pro Ala Glu Gln Thr Asn Ser Ser Glu
    605                 610                 615

CAA TCA AGT ACC GAT TCT AAA TCA AAC TAATTTTTA ATAACTTATA          2213
Gln Ser Ser Thr Asp Ser Lys Ser Asn
    620                 625

ATTATAAAAA ACCTAAACTT ATTTCAGTTT AGGTTTTTAT TTTCTAATTT            2263

CAAATTAGAA AATAAGACTT TCTAAAAAAG TCTTATTAAA ATGTTAAAAA            2313

AACCTTGTTT TTTATAGACT TTTTTAAATT TTTTATTATA ATATATAAGG            2363

AAAAATTTTA GTATTTCTGA CTGTGAAATT ATGAAGTTAA TAAAAATTGA            2413

AATTGAAGGT TTTAAATCCT TTGCTGAACC TGTAAGTATT AAATTTGATG            2463

GTTCAATTGT TGGAATAATT GGGCCAAATG GCTCTGGAAA ATCCAATATA            2513

AATGATGCAA TTAAATGAGT TTTAGGCGAA AAATCAGTTA AACAATTACG            2563

GGGCCAAAAT ATGGATGATG TCATTTTTGC TGGCTCAAAA ACAGTTATGC            2613

CTGTTAATAA AGCGATGGTA AAACTGACAT TTTTAGATGA AACTCGTGAA            2663

GATAGTGCC                                                         2672
```

Fig. 2A

```
Met Lys Lys Lys Ala Arg Lys Phe Leu Arg Leu Thr Ser Leu Thr Leu
1               5                   10                  15

Ala Pro Phe Ser Val Phe Thr Thr Leu Ile Ser Ala Gly Cys Leu Gln
            20                  25                  30

Lys Asn Ser Leu Leu Ser Glu Val Asn Tyr Leu Ala Leu Gly Asp Ser
        35                  40                  45

Leu Thr Ala Gly Phe Asn Glu Glu Thr Tyr Arg Asp Phe Gln Gly Thr
    50                  55                  60

Leu Asp Lys Asp Gly Asn Leu Ser Gly Gln Ser Tyr Pro Ala Tyr Phe
65                  70                  75                  80

Ala Tyr Tyr Leu Gln Lys Leu Asn Lys Asn Ser Leu Val Ser Tyr Asp
                85                  90                  95

Asn Leu Ala Ile Ser Gly Thr Thr Thr Glu Asn Trp Leu Tyr Leu Leu
            100                 105                 110

Asn Pro Thr Lys Tyr Pro Asn Gly Lys Met Ser Asp Asn Pro Leu Val
        115                 120                 125

Thr Asn Tyr Ser Gly Asn Glu Lys Tyr Asn Glu Ile Gly Ser Val Phe
    130                 135                 140

Gly Asp Phe Asn Lys Asp Ser Tyr Pro Gly Leu Val Glu Lys Val Lys
145                 150                 155                 160
```

MATCH WITH Fig. 2B

Fig. 2B

MATCH WITH Fig. 2A

```
Lys Ala Asn Leu Leu Thr Met Ser Val Gly Ala Asn Asp Pro Phe Leu
                165                 170                 175

Ala Ile Phe Asn Glu Phe Lys Lys Trp Ala Ser Ile Ile Lys Pro Lys
            180                 185                 190

Ser Glu Glu Ala Lys Lys Leu Leu Asp Pro Asn Glu Arg Ala Asn Phe
        195                 200                 205

Leu Ala Glu Lys Gly Met Leu Leu Lys Ala Glu Val Asn Lys Lys Ile
    210                 215                 220

Glu Glu Ile Asn Thr Asn Leu Asp Asn Leu Ile Lys Glu Leu Lys Ala
225                 230                 235                 240

Leu Asn Pro Lys Leu Ser Ile Asn Leu Val Gly Tyr Lys Leu Pro Asn
                245                 250                 255

Ser Gly Phe Ile Lys Ile Leu Lys Tyr Leu Leu Tyr Thr Tyr Ala Lys
            260                 265                 270

Ile Glu Thr Asp Phe Ile Asn Glu Ile Pro Glu Lys Ile Asn Lys Ile
        275                 280                 285

Ile Arg Glu Thr Ala Ile Lys Asn Lys Val Asn Tyr Ile Asp Val Tyr
    290                 295                 300

Asp Lys Ser Ile Trp Asn Asp Ser Asp Lys Asn Leu Met Ala Lys Asn
305                 310                 315                 320
```

MATCH WITH Fig. 2C

Fig. 2C

MATCH WITH Fig. 2B

| | | | | | | | | | | | | | | | |
|---|---|---|---|---|---|---|---|---|---|---|---|---|---|---|---|
| Phe | Asp | Phe | His | Pro | Ser | Ile | Gln | Gly | Tyr | Lys | Lys | Ile | Ala | His | Gln |
| | | | | 325 | | | | | 330 | | | | | 335 | |
| Leu | Leu | Leu | Lys | Leu | Thr | Leu | Asp | Gln | Glu | Glu | Lys | Asp | Asp | Ser | Asn |
| | | | 340 | | | | | 345 | | | | | 350 | | |
| Ala | Glu | Glu | Leu | Lys | Asn | Thr | Thr | Asn | Phe | Asp | Asp | Phe | Asp | Glu | Asn |
| | | 355 | | | | | 360 | | | | | 365 | | | |
| Lys | Pro | Thr | Tyr | Ser | Lys | Val | Ile | Asp | Leu | Ser | Val | Phe | Ala | Lys | Ser |
| | 370 | | | | | 375 | | | | | 380 | | | | |
| Asn | Lys | Glu | Phe | Leu | Glu | Lys | Leu | Asn | Glu | Asn | Lys | Gln | Thr | Ser | Glu |
| 385 | | | | | 390 | | | | | 395 | | | | | 400 |
| Phe | Ile | Ala | Gln | Lys | Ser | Thr | Phe | Asp | Thr | Asp | Gln | Glu | Ala | Ala | Ile |
| | | | | 405 | | | | | 410 | | | | | 415 | |
| Lys | Asp | Asp | Lys | Arg | Thr | Phe | Gly | Asn | Ile | Val | Arg | Glu | Ile | Val | Ser |
| | | | 420 | | | | | 425 | | | | | 430 | | |
| Leu | Pro | Ile | Phe | Asp | Asn | Phe | Asp | Phe | Arg | Glu | Leu | Ile | Pro | Val | Lys |
| | | 435 | | | | | 440 | | | | | 445 | | | |
| Asn | Pro | Phe | Val | Lys | Ala | Ile | Ile | Asn | Ser | Tyr | Leu | Gly | Lys | Pro | Ala |
| | 450 | | | | | 455 | | | | | 460 | | | | |
| Gly | Ser | Leu | Ile | Lys | Asp | Ile | Glu | Gln | Leu | Glu | Asn | Lys | Val | Lys | Asp |
| 465 | | | | | 470 | | | | | 475 | | | | | 480 |

MATCH WITH Fig. 2D

Fig. 2D

MATCH WITH Fig. 2C

```
Tyr Ala Arg Pro Asn Ile Lys Ile Phe Asp Thr Ile Ile Asp Ser Phe
                485                 490                 495

Ile Arg Lys Met Val Ala Phe Phe Ala Glu Leu Asn Thr Asp Gln Glu
            500                 505                 510

Ile Lys Glu Phe Lys Met Ser Pro Gln Ile Leu Phe Leu Thr Leu Arg
        515                 520                 525

Asn Ala Ile Leu Ser Pro Phe Asp Leu Thr Lys Leu Lys Asp Ser Ala
    530                 535                 540

Thr Phe Lys Ile Leu Met Asn Leu Lys Pro Glu Gln Ile Leu Thr Leu
545                 550                 555                 560

Leu Gly Leu Gly Lys Thr Pro Ser Val Pro Lys Pro Glu Lys Pro Lys
                565                 570                 575

Asp Gln Gly Ser Met Pro Gln Thr Asp Thr Ser Ser Gln Lys Gln Glu
            580                 585                 590

Ser Gly Thr Gly Ser Thr Asp Ser Thr Lys Ala Thr Thr Glu Asn Gln
        595                 600                 605

Lys Pro Ala Glu Gln Thr Asn Ser Ser Glu Gln Ser Ser Thr Asp Ser
    610                 615                 620

Lys Ser Asn
625
```

Purification of rP65

Recognition of Recombinant P65
By Postchallenge Swine Serum

Western blot probed with:

Solubility Properties of Authentic and Recombinant P65

TX-114 Fractionation and Western Blot probed with MAb to P65

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 2672 base pairs
( B ) TYPE: nucleic acid
( C ) STRANDEDNESS: single
( D ) TOPOLOGY: linear ( i i ) MOLECULE TYPE: genomic DNA
( A ) DESCRIPTION: region of 5.8 kb HindIII fragment from genomic library ( i i i ) HYPOTHETICAL: no ( i v ) ANTI-SENSE: no ( v ) FRAGMENT TYPE:

( v i ) ORIGINAL SOURCE:
( A ) ORGANISM: Mycoplasma hyopneumoniae
( B ) STRAIN: J
( C ) INDIVIDUAL ISOLATE:
( D ) DEVELOPMENTAL STAGE:
( E ) HAPLOTYPE:
( F ) TISSUE TYPE:
( G ) CELL TYPE: unicellular bacterium
( H ) CELL LINE:
( I ) ORGANELLE:

( v i i ) IMMEDIATE SOURCE:
( A ) LIBRARY: Genomic in γ Charon 4A, γ GEM12
( B ) CLONE: γMhpJ25, γMhpJ35, γMhpJG35, pZJ25, pZJ25.1, pZ125.14, pZJG35.1, pZJG35.12, pZJG35.13, pZJG35.14

( v i i i ) POSITION IN GENOME:
( A ) CHROMOSOME/SEGMENT: single chromosome
( B ) MAP POSITION: unknown
( C ) UNITS: unknown ( i x ) FEATURE:
( A ) NAME/KEY: sequence encodes entire 627 amino acids of the structural gene for the surface lipoprotein P65 and includes 312 bp upstream and 479 bp downstream of coding sequence
( B ) LOCATION: coding sequence for P65 spans 1881 bp of described sequence ( begins at nt 313 and includes all sequence through nt 2193)
( C ) IDENTIFICATION METHOD: by similarity to pattern of open reading frame; by experiment identifying protein products of sequence with immune serum to P65
( D ) OTHER INFORMATION: immunogenic surface lipoprotein of no known function; C- terminus exposed on external surface of cell ( x ) PUBLICATION INFORMATION:
( A ) AUTHORS: Mary F. Kim, Manijeh B. Heidari, Susan J. Stull, Mark A. McIntosh, and Kim S. Wise
( B ) TITLE: Identification and Mapping of an Immunogenic Region of Mycoplasma hyopneumoniae p65 Surface Lipoprotein Expressed in Escherichia coli from a Cloned Genomic Fragment
( C ) JOURNAL: Infection and Immunity
( D ) VOLUME: 58
( E ) ISSUE: 8
( F ) PAGES: 2637- 2643
( G ) DATE: August 1990
( H ) DOCUMENT NUMBER:
( I ) FILING DATE:
( J ) PUBLICATION DATE:
( K ) RELEVANT RESIDUES IN SEQ ID NO: From 1 to 2672

( x i ) SEQUENCE DESCRIPTION: SEQ ID NO:1:

```
AAGCTTGAGA AAATTACAAA AAAATTCATT TTCCAAAAAC GCTTTTAGCT          50

TTTATTAAAG GGCCCAAAGT TTTTAATGAA GTTCAAAATT GTAAAAATTG         100

TAATTATAAA ATCATTAAAG TTAATAATAA TATAAATAAA AAAATTTTTA         150

TCGCATTTAA ACAAGTTTCT TAATAATTTT GAATTTTAAT TTAGAAAATA         200

TAAAAATCTT GTTGATTTTT ATATAATTTT TTAACCTTTT TTTTTTTTTT         250

TTTTTTTTTA GGAATATGGT AAAATTTAGT CCATCTATCA AAAATATAGA         300

AAAGGAAAAA TT  ATG AAG AAA AAA GCA AGA AAA TTC TTA AGA CTA     345
               Met Lys Lys Lys Ala Arg Lys Phe Leu Arg Leu
               1               5                   10

ACT TCG CTT ACA CTA GCG CCT TTT TCG GTC TTC ACC ACT CTT ATT    390
Thr Ser Leu Thr Leu Ala Pro Phe Ser Val Phe Thr Thr Leu Ile
            15                  20                  25

TCA GCT GGT TGT TTG CAA AAA AAT TCT TTG CTT TCA GAA GTA AAT    435
Ser Ala Gly Cys Leu Gln Lys Asn Ser Leu Leu Ser Glu Val Asn
            30                  35                  40

TAT TTA GCC CTA GGT GAT TCA CTA ACA GCT GGA TTT AAT GAA GAA    480
Tyr Leu Ala Leu Gly Asp Ser Leu Thr Ala Gly Phe Asn Glu Glu
            45                  50                  55

ACA TAC CGT GAT TTT CAA GGT ACT TTA GAT AAA GAT GGT AAT TTA AGC    528
Thr Tyr Arg Asp Phe Gln Gly Thr Leu Asp Lys Asp Gly Asn Leu Ser
            60                  65                  70

GGT CAA TCT TAT CCT GCT TAT TTT GCT TAT TAT CTA CAA AAA CTT AAT    576
Gly Gln Ser Tyr Pro Ala Tyr Phe Ala Tyr Tyr Leu Gln Lys Leu Asn
        75                  80                      85
```

-continued

| | | | | | | | | | | | | | | | | |
|---|---|---|---|---|---|---|---|---|---|---|---|---|---|---|---|---|
| AAG | AAT | TCA | CTT | GTT | TCT | TAT | GAT | AAT | TTG | GCA | ATT | TCT | GGG | ACA | ACA | 624 |
| Lys | Asn | Ser | Leu | Val | Ser | Tyr | Asp | Asn | Leu | Ala | Ile | Ser | Gly | Thr | Thr | |
| | 90 | | | | | 95 | | | | | 100 | | | | | |
| ACA | GAA | AAC | TGA | CTT | TAC | CTT | CTT | AAT | CCA | ACC | AAA | TAT | CCA | AAT | GGA | 672 |
| Thr | Glu | Asn | Trp | Leu | Tyr | Leu | Leu | Asn | Pro | Thr | Lys | Tyr | Pro | Asn | Gly | |
| 105 | | | | | 110 | | | | | 115 | | | | | 120 | |
| AAA | ATG | AGC | GAT | AAT | CCG | TTA | GTT | ACA | AAC | TAT | TCA | GGA | AAT | GAA | AAA | 720 |
| Lys | Met | Ser | Asp | Asn | Pro | Leu | Val | Thr | Asn | Tyr | Ser | Gly | Asn | Glu | Lys | |
| | | | | 125 | | | | | 130 | | | | | 135 | | |
| TAT | AAT | GAA | ATA | GGC | TCT | GTT | TTT | GGT | GAT | TTT | AAT | AAG | GAT | TCC | TAT | 768 |
| Tyr | Asn | Glu | Ile | Gly | Ser | Val | Phe | Gly | Asp | Phe | Asn | Lys | Asp | Ser | Tyr | |
| | | | 140 | | | | | 145 | | | | | 150 | | | |
| CCT | GGT | TTA | GTC | GAA | AAA | GTT | AAA | AAA | GCA | AAC | CTT | TTG | ACA | ATG | TCA | 816 |
| Pro | Gly | Leu | Val | Glu | Lys | Val | Lys | Lys | Ala | Asn | Leu | Leu | Thr | Met | Ser | |
| | | 155 | | | | | 160 | | | | | 165 | | | | |
| GTG | GGA | GCT | AAC | GAT | CCT | TTT | TTA | GCA | ATT | TTT | AAT | GAA | TTT | AAA | AAA | 864 |
| Val | Gly | Ala | Asn | Asp | Pro | Phe | Leu | Ala | Ile | Phe | Asn | Glu | Phe | Lys | Lys | |
| | 170 | | | | | 175 | | | | | 180 | | | | | |
| TGA | GCA | AGT | ATA | ATA | AAA | CCA | AAA | TCA | GAG | GAA | GCA | AAA | AAA | TTA | CTA | 912 |
| Trp | Ala | Ser | Ile | Ile | Lys | Pro | Lys | Ser | Glu | Glu | Ala | Lys | Lys | Leu | Leu | |
| 185 | | | | | 190 | | | | | 195 | | | | | 200 | |
| GAT | CCA | AAT | GAA | AGA | GCG | AAT | TTC | CTA | GCA | GAA | AAA | GGA | ATG | CTT | TTA | 960 |
| Asp | Pro | Asn | Glu | Arg | Ala | Asn | Phe | Leu | Ala | Glu | Lys | Gly | Met | Leu | Leu | |
| | | | | 205 | | | | | 210 | | | | | 215 | | |
| AAG | GCG | GAA | GTT | AAT | AAA | AAA | ATT | GAG | GAA | ATA | AAC | ACA | AAT | CTT | GAT | 1008 |
| Lys | Ala | Glu | Val | Asn | Lys | Lys | Ile | Glu | Glu | Ile | Asn | Thr | Asn | Leu | Asp | |
| | | | 220 | | | | | 225 | | | | | 230 | | | |
| AAT | TTA | ATT | AAA | GAA | TTA | AAG | GCG | CTT | AAT | CCA | AAA | TTA | AGT | ATA | AAT | 1056 |
| Asn | Leu | Ile | Lys | Glu | Leu | Lys | Ala | Leu | Asn | Pro | Lys | Leu | Ser | Ile | Asn | |
| | | 235 | | | | | 240 | | | | | 245 | | | | |
| TTA | GTT | GGA | TAT | AAA | TTG | CCA | AAT | TCC | GGT | TTT | ATT | AAG | ATT | TTA | AAG | 1104 |
| Leu | Val | Gly | Tyr | Lys | Leu | Pro | Asn | Ser | Gly | Phe | Ile | Lys | Ile | Leu | Lys | |
| | 250 | | | | | 255 | | | | | 260 | | | | | |
| TAT | CTT | TTA | TAT | ACT | TAT | GCA | AAA | ATT | GAA | ACG | GAC | TTT | ATC | AAT | GAA | 1152 |
| Tyr | Leu | Leu | Tyr | Thr | Tyr | Ala | Lys | Ile | Glu | Thr | Asp | Phe | Ile | Asn | Glu | |
| 265 | | | | | 270 | | | | | 275 | | | | | 280 | |
| ATT | CCC | GAA | AAA | ATT | AAC | AAA | ATT | ATT | CGT | GAA | ACC | GCC | ATT | AAA | AAT | 1200 |
| Ile | Pro | Glu | Lys | Ile | Asn | Lys | Ile | Ile | Arg | Glu | Thr | Ala | Ile | Lys | Asn | |
| | | | | 285 | | | | | 290 | | | | | 295 | | |
| AAG | GTA | AAT | TAT | ATT | GAT | GTC | TAT | GAT | AAA | AGT | ATT | TGA | AAT | GAT | TCT | 1248 |
| Lys | Val | Asn | Tyr | Ile | Asp | Val | Tyr | Asp | Lys | Ser | Ile | Trp | Asn | Asp | Ser | |
| | | | 300 | | | | | 305 | | | | | 310 | | | |
| GAT | AAA | AAT | TTA | ATG | GCG | AAA | AAT | TTT | GAC | TTC | CAC | CCT | TCA | ATT | CAA | 1296 |
| Asp | Lys | Asn | Leu | Met | Ala | Lys | Asn | Phe | Asp | Phe | His | Pro | Ser | Ile | Gln | |
| | | 315 | | | | | 320 | | | | | 325 | | | | |
| GGT | TAT | AAA | AAA | ATT | GCT | CAC | CAA | CTT | TTG | TTA | AAA | TTA | ACT | CTT | GAC | 1344 |
| Gly | Tyr | Lys | Lys | Ile | Ala | His | Gln | Leu | Leu | Leu | Lys | Leu | Thr | Leu | Asp | |
| | 330 | | | | | 335 | | | | | 340 | | | | | |
| CAA | GAA | GAA | AAA | GAT | GAT | TCT | AAT | GCT | GAA | GAG | CTA | AAA | AAT | ACT | ACA | 1392 |
| Gln | Glu | Glu | Lys | Asp | Asp | Ser | Asn | Ala | Glu | Glu | Leu | Lys | Asn | Thr | Thr | |
| 345 | | | | | 350 | | | | | 355 | | | | | 360 | |
| AAT | TTC | GAT | GAT | TTT | GAT | GAG | AAT | AAA | CCG | ACC | TAT | TCC | AAA | GTT | ATT | 1440 |
| Asn | Phe | Asp | Asp | Phe | Asp | Glu | Asn | Lys | Pro | Thr | Tyr | Ser | Lys | Val | Ile | |
| | | | | 365 | | | | | 370 | | | | | 375 | | |
| GAC | CTA | AGT | GTT | TTT | GCA | AAA | TCA | AAT | AAA | GAA | TTT | CTT | GAA | AAA | TTA | 1488 |
| Asp | Leu | Ser | Val | Phe | Ala | Lys | Ser | Asn | Lys | Glu | Phe | Leu | Glu | Lys | Leu | |
| | | | 380 | | | | | 385 | | | | | 390 | | | |
| AAC | GAA | AAT | AAG | CAA | ACT | AGT | GAA | TTT | ATT | GCT | CAA | AAA | TCC | ACT | TTT | 1536 |
| Asn | Glu | Asn | Lys | Gln | Thr | Ser | Glu | Phe | Ile | Ala | Gln | Lys | Ser | Thr | Phe | |
| | | 395 | | | | | 400 | | | | | 405 | | | | |

-continued

```
GAC ACC GAT CAA GAA GCT GCA ATC AAA GAC GAC AAA CGC ACT TTT          1581
Asp Thr Asp Gln Glu Ala Ala Ile Lys Asp Asp Lys Arg Thr Phe
    410                 415                 420

GGA AAT ATA GTT CGA GAA ATT GTA TCT TTA CCA ATC TTC GAT AAT          1626
Gly Asn Ile Val Arg Glu Ile Val Ser Leu Pro Ile Phe Asp Asn
    425                 430                 435

TTT GAT TTT AGA GAG TTA ATA CCT GTT AAA AAT CCA TTT GTA AAA          1671
Phe Asp Phe Arg Glu Leu Ile Pro Val Lys Asn Pro Phe Val Lys
    440                 445                 450

GCA ATT ATT AAC AGC TAT TTA GGG AAA CCA GCT GGT TCT CTT ATA          1716
Ala Ile Ile Asn Ser Tyr Leu Gly Lys Pro Ala Gly Ser Leu Ile
    455                 460                 465

AAA GAT ATC GAA CAA CTC GAA AAT AAA GTG AAA GAT TAC GCA AGA          1761
Lys Asp Ile Glu Gln Leu Glu Asn Lys Val Lys Asp Tyr Ala Arg
    470                 475                 480

CCT AAT ATC AAG ATT TTC GAT ACA ATT ATT GAC TCA TTC ATA AGA          1806
Pro Asn Ile Lys Ile Phe Asp Thr Ile Ile Asp Ser Phe Ile Arg
    485                 490                 495

AAA ATG GTA GCA TTT TTT GCT GAA TTA AAC ACT GAT CAA GAA ATA          1851
Lys Met Val Ala Phe Phe Ala Glu Leu Asn Thr Asp Gln Glu Ile
    500                 505                 510

AAA GAA TTC AAA ATG TCA CCT CAA ATA CTA TTT CTG ACA CTA AGA          1896
Lys Glu Phe Lys Met Ser Pro Gln Ile Leu Phe Leu Thr Leu Arg
    515                 520                 525

AAT GCA ATA CTA AGT CCA TTT GAT TTA ACT AAA TTA AAA GAC AGT          1941
Asn Ala Ile Leu Ser Pro Phe Asp Leu Thr Lys Leu Lys Asp Ser
    530                 535                 540

GCT ACA TTT AAA ATT TTA ATG AAT CTC AAA CCA GAA CAA ATA TTA          1986
Ala Thr Phe Lys Ile Leu Met Asn Leu Lys Pro Glu Gln Ile Leu
    545                 550                 555

ACT CTA CTA GGC CTA GGT AAA ACC CCT TCA GTT CCT AAA CCT GAA          2031
Thr Leu Leu Gly Leu Gly Lys Thr Pro Ser Val Pro Lys Pro Glu
    560                 565                 570

AAA CCA AAA GAT CAA GGT TCT ATG CCA CAA ACA GAT ACT TCT AGT          2076
Lys Pro Lys Asp Gln Gly Ser Met Pro Gln Thr Asp Thr Ser Ser
    575                 580                 585

CAA AAA CAA GAA AGC GGA ACA GGT TCA ACA GAT TCA ACA AAA GCT          2121
Gln Lys Gln Glu Ser Gly Thr Gly Ser Thr Asp Ser Thr Lys Ala
    590                 595                 600

ACA ACT GAA AAC CAA AAA CCA GCT GAG CAA ACA AAT TCT TCT GAG          2166
Thr Thr Glu Asn Gln Lys Pro Ala Glu Gln Thr Asn Ser Ser Glu
    605                 610                 615

CAA TCA AGT ACC GAT TCT AAA TCA AAC TAATTTTTA ATAACTTATA             2213
Gln Ser Ser Thr Asp Ser Lys Ser Asn
    620                 625

ATTATAAAAA ACCTAAACTT ATTTCAGTTT AGGTTTTTAT TTTCTAATTT               2263

CAAATTAGAA AATAAGACTT TCTAAAAAAG TCTTATTAAA ATGTTAAAAA               2313

AACCTTGTTT TTTATAGACT TTTTTAAATT TTTTATTATA ATATATAAGG               2363

AAAAATTTTA GTATTTCTGA CTGTGAAATT ATGAAGTTAA TAAAAATTGA               2413

AATTGAAGGT TTTAAATCCT TTGCTGAACC TGTAAGTATT AAATTTGATG               2463

GTTCAATTGT TGGAATAATT GGGCCAAATG GCTCTGGAAA ATCCAATATA               2513

AATGATGCAA TTAAATGAGT TTTAGGCGAA AAATCAGTTA AACAATTACG               2563

GGGCCAAAAT ATGGATGATG TCATTTTTGC TGGCTCAAAA ACAGTTATGC               2613

CTGTTAATAA AGCGATGGTA AAACTGACAT TTTTAGATGA AACTCGTGAA               2663

GATAGTGCC                                                            2672
```

( 2 ) INFORMATION FOR SEQ ID NO:2:

( i ) SEQUENCE CHARACTERISTICS:
( A ) LENGTH: 627 amino acid residues
( B ) TYPE: amino acid
( C ) STRANDEDNESS:
( D ) TOPOLOGY: linear ( i i ) MOLECULE TYPE: protein
( A ) DESCRIPTION: predicted amino acid sequence of complete 627 residues of the P65 lipoprotein, derived from the nucleic acid sequence ( i i i ) HYPOTHETICAL: no ( i v ) ANTI-SENSE: no ( v ) FRAGMENT TYPE: whole polypeptide ( v i ) ORIGINAL SOURCE:
( A ) ORGANISM: Mycoplasma hyopneumoniae
( B ) STRAIN: J
( C ) INDIVIDUAL ISOLATE:
( D ) DEVELOPMENTAL STAGE:
( E ) HAPLOTYPE:
( F ) TISSUE TYPE:
( G ) CELL TYPE: unicellular bacterium
( H ) CELL LINE:
( I ) ORGANELLE:

( v i i ) IMMEDIATE SOURCE:
( A ) LIBRARY: Genomic in γ Charon 4A, γ GEM12
( B ) CLONE: γMhpJ25, γMhpJ35, γMhpJG35, pZJ25, pZJ25.1, pZJ25.14, pZJG35.1, pZJG35.12, pZJG35.13, pZJG35.14

( v i i i ) POSITION IN GENOME:
( A ) CHROMOSOME/SEGMENT: single chromosome
( B ) MAP POSITION: unknown
( C ) UNITS: unknown ( i x ) FEATURE:
( A ) NAME/KEY: 627 amino acid sequence representing complete sequence (including signal sequence) of surface lipoprotein P65
( B ) LOCATION: entire derived coded sequence
( C ) IDENTIFICATION METHOD: clone identified by immuno-detection of protein product with antiserum specific for P65; residue sequence deduced from nucleic acid sequence
( D ) OTHER INFORMATION: immunogenic surface lipoprotein of no known function; C- terminus exposed on external surface of cell; N-terminal signal sequence (first 29 amino acid residues) cleaved during lipid modification process ( x ) PUBLICATION INFORMATION:
( A ) AUTHORS: Mary F. Kim, Manijeh B. Heidari, Susan J. Stull, Mark A. McIntosh, and Kim S. Wise
( B ) TITLE: Identification and Mapping of an Immunogenic Region of Mycoplasma hyopneumoniae p65 Surface Lipoprotein Expressed in Escherichia coli from a Cloned Genomic Fragment
( C ) JOURNAL: Infection and Immunity
( D ) VOLUME: 58
( E ) ISSUE: 8
( F ) PAGES: 2637- 2643
( G ) DATE: August 1990
( H ) DOCUMENT NUMBER:
( I ) FILING DATE:
( J ) PUBLICATION DATE:

( K ) RELEVANT RESIDUES IN SEQ ID NO: From 1 to 627

( x i ) SEQUENCE DESCRIPTION: SEQ ID NO: 2:

Met Lys Lys Lys Ala Arg Lys Phe Leu Arg Leu Thr Ser Leu Thr Leu
1 5 10 15

Ala Pro Phe Ser Val Phe Thr Thr Leu Ile Ser Ala Gly Cys Leu Gln
20 25 30

Lys Asn Ser Leu Leu Ser Glu Val Asn Tyr Leu Ala Leu Gly Asp Ser
35 40 45

Leu Thr Ala Gly Phe Asn Glu Glu Thr Tyr Arg Asp Phe Gln Gly Thr
50 55 60

Leu Asp Lys Asp Gly Asn Leu Ser Gly Gln Ser Tyr Pro Ala Tyr Phe
65 70 75 80

Ala Tyr Tyr Leu Gln Lys Leu Asn Lys Asn Ser Leu Val Ser Tyr Asp
85 90 95

Asn Leu Ala Ile Ser Gly Thr Thr Thr Glu Asn Trp Leu Tyr Leu Leu
100 105 110

Asn Pro Thr Lys Tyr Pro Asn Gly Lys Met Ser Asp Asn Pro Leu Val
115 120 125

Thr Asn Tyr Ser Gly Asn Glu Lys Tyr Asn Glu Ile Gly Ser Val Phe
130 135 140

Gly Asp Phe Asn Lys Asp Ser Tyr Pro Gly Leu Val Glu Lys Val Lys
145 150 155 160

Lys Ala Asn Leu Leu Thr Met Ser Val Gly Ala Asn Asp Pro Phe Leu
165 170 175

Ala Ile Phe Asn Glu Phe Lys Lys Trp Ala Ser Ile Ile Lys Pro Lys
180 185 190

Ser Glu Glu Ala Lys Lys Leu Leu Asp Pro Asn Glu Arg Ala Asn Phe
195 200 205

Leu Ala Glu Lys Gly Met Leu Leu Lys Ala Glu Val Asn Lys Lys Ile
210 215 220

Glu Glu Ile Asn Thr Asn Leu Asp Asn Leu Ile Lys Glu Leu Lys Ala
225 230 235 240

Leu Asn Pro Lys Leu Ser Ile Asn Leu Val Gly Tyr Lys Leu Pro Asn
245 250 255

Ser Gly Phe Ile Lys Ile Leu Lys Tyr Leu Leu Tyr Thr Tyr Ala Lys
260 265 270

Ile Glu Thr Asp Phe Ile Asn Glu Ile Pro Glu Lys Ile Asn Lys Ile
275 280 285

Ile Arg Glu Thr Ala Ile Lys Asn Lys Val Asn Tyr Ile Asp Val Tyr
290 295 300

Asp Lys Ser Ile Trp Asn Asp Ser Asp Lys Asn Leu Met Ala Lys Asn
305 310 315 320

Phe Asp Phe His Pro Ser Ile Gln Gly Tyr Lys Lys Ile Ala His Gln
325 330 335

Leu Leu Leu Lys Leu Thr Leu Asp Gln Glu Glu Lys Asp Asp Ser Asn
340 345 350

Ala Glu Glu Leu Lys Asn Thr Thr Asn Phe Asp Asp Phe Asp Glu Asn
355 360 365

Lys Pro Thr Tyr Ser Lys Val Ile Asp Leu Ser Val Phe Ala Lys Ser
370 375 380

Asn Lys Glu Phe Leu Glu Lys Leu Asn Glu Asn Lys Gln Thr Ser Glu
385 390 395 400

Phe Ile Ala Gln Lys Ser Thr Phe Asp Thr Asp Gln Glu Ala Ala Ile

-continued

| | | | | | | | | | | | | | | | |
|---|---|---|---|---|---|---|---|---|---|---|---|---|---|---|---|
| | | | | 405 | | | | | 410 | | | | | 415 | |
| Lys | Asp | Asp | Lys | Arg | Thr | Phe | Gly | Asn | Ile | Val | Arg | Glu | Ile | Val | Ser |
| | | | 420 | | | | | 425 | | | | | 430 | | |
| Leu | Pro | Ile | Phe | Asp | Asn | Phe | Asp | Phe | Arg | Glu | Leu | Ile | Pro | Val | Lys |
| | | 435 | | | | | 440 | | | | | 445 | | | |
| Asn | Pro | Phe | Val | Lys | Ala | Ile | Ile | Asn | Ser | Tyr | Leu | Gly | Lys | Pro | Ala |
| | 450 | | | | | 455 | | | | | 460 | | | | |
| Gly | Ser | Leu | Ile | Lys | Asp | Ile | Glu | Gln | Leu | Glu | Asn | Lys | Val | Lys | Asp |
| 465 | | | | | 470 | | | | | 475 | | | | | 480 |
| Tyr | Ala | Arg | Pro | Asn | Ile | Lys | Ile | Phe | Asp | Thr | Ile | Ile | Asp | Ser | Phe |
| | | | | 485 | | | | | 490 | | | | | 495 | |
| Ile | Arg | Lys | Met | Val | Ala | Phe | Phe | Ala | Glu | Leu | Asn | Thr | Asp | Gln | Glu |
| | | | 500 | | | | | 505 | | | | | 510 | | |
| Ile | Lys | Glu | Phe | Lys | Met | Ser | Pro | Gln | Ile | Leu | Phe | Leu | Thr | Leu | Arg |
| | | 515 | | | | | 520 | | | | | 525 | | | |
| Asn | Ala | Ile | Leu | Ser | Pro | Phe | Asp | Leu | Thr | Lys | Leu | Lys | Asp | Ser | Ala |
| | 530 | | | | | 535 | | | | | 540 | | | | |
| Thr | Phe | Lys | Ile | Leu | Met | Asn | Leu | Lys | Pro | Glu | Gln | Ile | Leu | Thr | Leu |
| 545 | | | | | 550 | | | | | 555 | | | | | 560 |
| Leu | Gly | Leu | Gly | Lys | Thr | Pro | Ser | Val | Pro | Lys | Pro | Glu | Lys | Pro | Lys |
| | | | | 565 | | | | | 570 | | | | | 575 | |
| Asp | Gln | Gly | Ser | Met | Pro | Gln | Thr | Asp | Thr | Ser | Ser | Gln | Lys | Gln | Glu |
| | | | 580 | | | | | 585 | | | | | 590 | | |
| Ser | Gly | Thr | Gly | Ser | Thr | Asp | Ser | Thr | Lys | Ala | Thr | Thr | Glu | Asn | Gln |
| | | 595 | | | | | 600 | | | | | 605 | | | |
| Lys | Pro | Ala | Glu | Gln | Thr | Asn | Ser | Ser | Glu | Gln | Ser | Ser | Thr | Asp | Ser |
| | 610 | | | | | 615 | | | | | 620 | | | | |
| Lys | Ser | Asn | | | | | | | | | | | | | |
| 625 | | | | | | | | | | | | | | | |

DNA SEQUENCES CODING FOR *MYCOPLASMA HYOPNEUMONIAE* SURFACE ANTIGENS, CORRESPONDING PROTEINS AND USE IN VACCINES AND DIAGNOSTIC PROCEDURES

This is a continuation of application Ser. No. 08/373,957, Jan. 17, 1995 now abandoned.

BACKGROUND OF THE INVENTION

1. Field of the Invention

The present invention relates to *Mycoplasma hyopneumoniae* P65 surface antigen, a lipoprotein capable of eliciting an antibody or other immune response which selectively recognizes an epitope(s) of P65, to such antigens prepared by recombinant DNA methods, to swine mycoplasma vaccine based on such antigens, to methods of treating swine to prevent enzootic pneumonia using that vaccine, and to diagnostic tests for detecting the presence of swine mycoplasma infections in swine herds.

2. Brief Description of the Prior Art

Enzootic pneumonia in swine is caused by *Mycoplasma hyopneumoniae*. The disease is transmitted from pig to pig through the nasal passages by airborne organisms expelled from the lungs of infected pigs. The primary infection by *Mycoplasma hyorneumoniae* may be followed by secondary infection by other mycoplasma species (*Mycoplasma hyorhinis* and *Mycoplasma flocculare*) as well as bacterial pathogens. The disease rarely causes death but causes decreased growth and weight gain.

*Mycoplasma hyopneumoniae* is a small, prokaroytic microbe smaller and simpler in structure than bacteria, but more complex than viruses. Unlike viruses, they are capable of a free living existence, through they are often found in association with eukaroytic cells as they have absolute requirements for exogenous sterols and fatty acids which generally necessitates growth in serum-containing media. *Mycoplasma hyopneumoniae* is bounded by a cell membrane but not by a cell wall. They have an extremely small genome, approximately 750,000 base pairs in length.

Due to the serious economic consequences of pig pneumonia, vaccines against *Mycoplasma hyopneumoniae* and diagnostic testing methods which will indicate the presence of an infection have been sought. Vaccines containing preparations of mycoplasma organisms grown in broth medium have been marketed. However, the requirement for serum in growth medium adds great expense to the process and introduces possible concerns regarding adverse reactions induced by serum components present in the immunizing material. Cost effective production of the appropriate recombinant mycoplasma protein in the absence of serum offers an improvement in terms of economy and vaccine safety. Such a recombinant protein also offers a specific target for recognition of antibodies to the organisms, which may detect infection with this agent. Current serologic assays for detection are confounded by non-specific reactions due to the antigenic cross-reactivity of multiple common swine mycoplasmas.

In earlier work, certain lipoproteins present on the cellular membrane of *Mycoplasma hyopneumoniae* were identified as mediating or inducing immunological reactions (Kim, M. F., M. B. Heidari, S. J. Stull, M. A. McIntosh, and K. S. Wise. 1990. Infect. Immun. 58:2637–2643; Wise, K. S., and M. F. Kim. 1987 J. Bacteriol. 169:5546–5555). From those lipoproteins, P65 was shown to be capable of eliciting an antibody which selectively recognized an epitope(s) of P65 without unwanted cross-reactions with antibodies to other mycoplasmas, especially *Mycoplasma flocculare*. P65 was shown to be integrally associated with the cell membrane and covalently linked to a lipid moiety, with the majority of the protein, including the C-terminus, exposed to the exterior of the cell, consistent with the predicted orientation of surface lipoproteins which are anchored by N-terminal lipid moieties.

While P65 was an attractive candidate for developing a recombinant protein because of its ability to elicit an antibody which is selective for *Mycoplasma hyooneumoniae*, attempts to determine the amino acid sequences failed because of N-terminal blocking by the lipid and isolation of internal fragments has been problematic. Functional analyses have been similarly unrewarding because of the attached lipid which renders P65 extremely hydrophobic making detergents an absolute requirement for solubilization which essentially precludes tests on viable cells or those tests involving aqueous buffer systems.

Determining and utilizing the DNA sequence coding for P65 has also been very difficult, despite the small size of the mycoplasma chromosome, because of a lack of vehicles for mobilizing and transferring DNA into these organisms (Kim et al, 1990, supra) and because of inherent problems in the expression of mycoplasma genes in more versatile, heterologous hosts such as *E. coli*. *Mycoplasma hyopneumoniae* uses an alternative genetic code (in which the UGA translation termination codon is used to encode tryptophan) and expression of mycoplasma genes in *E. coli* is complicated by truncation of products at the UGA codons. In addition, expression of partial products occurs through promiscuous translation from multiple, unpredictable sites in structural genes, a phenomenon that is probably common among most mycoplasmas (Notarnicola, S. N., M. A. McIntosh, and K. S. Wise. 1990. J. Bacteriol. 172:2986–2995).

SUMMARY OF THE INVENTION

In view of the above, the present invention relates to a DNA sequence shown in FIG. 1. The invention also relates to a biologically active fragment of said DNA sequence which encodes at least one protein which is capable of eliciting an antibody or other immune response which recognizes an epitope(s) of P65 and to a biologically active mutant of said DNA sequence which encodes at least one protein which is capable of eliciting an antibody or other immune response which recognizes an epitope(s) of P65. The subject DNA sequence may encode a protein which is the entire antigen, or a fragment or derivative of the antigen or a fusion product of the antigen or fragment and another protein, provided that the protein which is produced from such DNA sequence is capable of eliciting an antibody or other immune response which recognizes an epitope(s)of P65.

The present invention also concerns an essentially pure protein having a sequence coded by any of the DNA sequences described above, including the sequence shown in FIG. 2; an expression vector containing a promoter, a non-coding sequence and any of the coding DNA sequences described above and a host transformed with said expression vector; a vaccine containing a protein having a sequence coded by any of the DNA sequences described above; a diagnostic procedure based on those proteins or antibodies raised against them for detecting the presence of *Mycoplasma hyopneumoniae* infections in swine herds, and a diagnostic procedure utilizing any portion of said DNA sequence shown in FIG. 1 or an RNA equivalent thereof in RNA form to detect the presence of the gene or organism in swine-derived material by methods of synthesis, amplification or hybridization of nucleic acid sequences.

The invention summarized above comprises the DNA and protein sequences, etc. hereinafter described, the scope of the invention being indicated by the subjoined claims.

BRIEF DESCRIPTION OF THE DRAWINGS

FIG. 1A–1G depicts the DNA sequence encoding the entire 627 amino acids of the structural gene for the surface lipoprotein P65 from *Mycoplasma hyopneumoniae* and includes 312 base pairs upstream and 479 base pairs downstream of the coding sequence. The DNA sequence in the coding sequence is divided into three base codons which align with the proper reading frame of the gene. SEQ ID NO:1 The amino acid sequence (lower line) is the translation of the DNA codon directly above with all UGA codons assigned as tryptophan.

FIG. 2A–2D depicts the amino acid sequence of the intact surface lipoprotein P65. SEQ ID NO:2

DETAILED DESCRIPTION OF THE INVENTION

Figure 3:
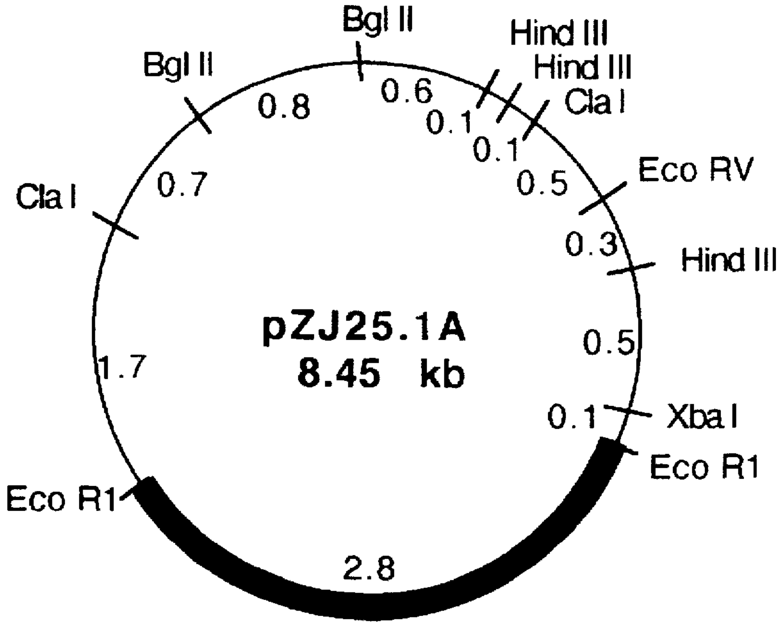
FIG. 3 is a diagram of plasmid pZJ25.1A. The hatched region represents a DNA sequence responsible for the expression of a polypeptide (P19) carrying epitopes related to P65.

Reference will now be made in detail to the presently preferred embodiments of the invention, which, together with the drawings and the following examples, serve to explain the principles of the invention. All references discussed in this specification are hereby incorporated in their entirety by reference. The three letter designations for amino acids used in this application are as follows:

| AMINO ACID | THREE-LETTER ABBREVIATION |
|---|---|
| Alanine | Ala |
| Arginine | Arg |
| Asparagine | Asn |
| Aspartic acid | Asp |
| Cysteine | Cys |
| Glutamine | Gln |
| Glutamic acid | Glu |
| Glycine | Gly |
| Histidine | His |
| Isoleucine | Ile |
| Leucine | Leu |
| Lysine | Lys |
| Methionine | Met |
| Phenylalanine | Phe |
| Proline | Pro |
| Serine | Ser |
| Threonine | Thr |
| Tryptophan | Trp |
| Tyrosine | Tyr |
| Valine | Val |

As noted above, the present invention relates to a recombinant DNA sequence between base pairs 313 and 2193 as shown in FIG. 1, (SEQ ID NO:1) the complete 2672 sequence illustrating the entire structural gene for *Mycoplasma hyopneumoniae* P65 including its hydrophobic lipid-modified N-terminal end. More generally, the invention concerns any DNA sequence coding for a protein which is capable of eliciting an antibody or other immune response (e.g., T-cell response of the immune system) which recognizes an epitope(s) of the amino acid sequence depicted in FIG. 2 (SEQ ID NO:2), including less than the full DNA sequence and mutants thereof. Hence the DNA sequence may encode a protein which is the entire antigen between base pairs 313 and 2193, or a fragment or derivative of the antigen or a fusion product of the antigen or fragment and another protein, provided that the protein which is produced from such DNA sequence is capable of eliciting an antibody or other immune response which recognizes an epitope(s) of the amino acid sequence depicted in FIG. 2.

As a result, the term "DNA sequence coding for a protein which is capable of eliciting an antibody or other immune response which recognizes an epitope(s) of the amino acid sequence depicted in FIG. 2" (SEQ ID NO:2) encompasses DNA sequences which encode for and/or express in appropriate transformed cells, proteins which may be the full length antigen, antigen fragment, antigen derivative or a fusion product of such antigen, antigen fragment or antigen derivative with another protein. Included antigen derivatives include those where UGA codons have been converted into codons recognized by the host as non stop codons, most commonly UGG.

Proteins included within the present invention have an amino acid sequence depicted in FIG. 2 (SEQ ID NO:2). Other included proteins consist of a fragment of said sequence capable of eliciting an antibody or other immune response which recognizes an epitope(s) of the amino acid sequence depicted in FIG. 2 (SEQ ID NO:2) and a mutuant of said sequence capable of eliciting an antibody or other immune response which recognizes an epitope(s) of the amino acid sequence depicted in FIG. 2 (SEQ ID NO:2).

The appropriate DNA sequence may be inserted into any of a wide variety of expression vectors by a variety of procedures, in general, through an appropriate restriction endonuclease site. Such procedures and others are deemed to be known by those skilled in the art. Suitable vectors include chromosomal, nonchromosomal and synthetic DNA sequences; e.g., derivatives of SV40; bacterial plasmids; phage DNAs; yeast plasmids; vectors derived from combinations of plasmids and phage DNAs, viral DNA such as baculovirus, vaccinia, adenovirus, fowl pox virus, pseudorabies, etc. The appropriate DNA sequence must be operatively linked in the vector to an appropriate expression control sequence(s) (promoter) to direct mRNA synthesis. As representative examples of such promoters, there may be mentioned LTR or SV40 promoter, the *E. coli lac* or *trp*, the phage lambda PL promoter and other promoters known to control expression of genes in prokaryotic and eukaryotic cells or their viruses. The expression vector also includes a non-coding sequence for a ribosome binding site for translation initiation and a transcription terminator. The vector may also include appropriate sequences for amplifying expression.

The vector containing the appropriate DNA sequence as hereinabove described, as well as an appropriate promoter or control sequence, may be employed to transform an appropriate host to permit the host to express the protein. Examples of host organisms and cells include bacterial strains (e.g., *E. coli*, Pseudomonas, Bacillus, Salmonella, etc.), fungi (e.g., yeasts and other fungi), animal or plant hosts (e.g., mouse, swine or animal and human tissue cells). The selection of the host is deemed to be within the scope of those skilled in the art.

It is also understood that the appropriate DNA sequence present in the vector when introduced into a host may express part or only a portion of the protein which is encoded within the noted terminology, it being sufficient that the expressed protein be capable of eliciting an antibody or other immune response which recognizes an epitope(s) of the amino acid sequence depicted in FIG. 2 (SEQ ID NO:2). For example, in employing *E. coli* as a host organism, the UGA codon is a stop codon so that the expressed protein may only be a fragment of the antigen encoded into the vector and for this reason it is generally preferred that all of the UGA codons in the appropriate DNA sequence be converted into non stop codons. Another way around the problem in a host that recognizes UGA as a stop codon is to include an additional DNA sequence which encode a t-RNA which translates the UGA codon within a protein coding sequence as tryptophan in the transformed organism.

The protein expressed by the host transformed by the vector containing the appropriate DNA sequence containing one or more proteins which are capable of eliciting an antibody or other immune response which recognizes an epitope(s) of the amino acid sequence depicted in FIG. 2 (SEQ ID NO:2) may be harvested by methods which will occur to those skilled in the art and used in a vaccine for protection of a non-human animal, such as a bovine, swine, etc., against mycoplasmal pneumonia caused by *Mycoplasma hyopneumoniae*. Said one or more proteins which are capable of eliciting an antibody or other immune response which recognizes an epitope(s) of the amino acid sequence depicted in FIG. 2 (SEQ ID NO:2) are used in an amount effective to provide protection against mycoplasmal pneumonia caused by *Mycoplasma hyopneumoniae* and may be used in combination with a suitable physiologically acceptable carrier.

The term "protecting" or "protection" when used with respect to the vaccine for mycoplasmal pneumonia caused by *Mycoplasma hyopneumoniae* described herein means that the vaccine prevents mycoplasmal pneumonia caused by *Mycoplasma hyopneumoniae* or reduces the severity of the disease.

The carrier which is employed in conjunction with the protein antigen may be any one of a wide variety of carriers. As representative examples of suitable carriers, there may be mentioned mineral oil, synthetic polymers, etc. Carriers for vaccines are well known in the art and the selection of a suitable carrier is deemed to be within the scope of those skilled in the art. The selection of a suitable carrier is also dependent upon the manner in which the vaccine is to be administered.

The present invention provides a method of immunizing a susceptible non-human animal, e.g., swine, bovine, etc., against mycoplasmal pneumonia caused by *Mycoplasma hyopneumoniae* with the vaccine described above. For purposes of this invention, the vaccine is administered in an effective amount. The vaccine may be administered by any of the methods well known to those skilled in the art, for example, by intramuscular, subcutaneous, intraperitoneal or intravenous injection. Alternatively, the vaccine may be administered intranasally or orally. It is also to be understood that the vaccine may include active components or adjuvants in addition to the antigen(s) or fragments hereinabove described.

The host expressing the antigen may itself be used to deliver antigen to non-human animals, by introducing killed or viable host cells that are capable of propagating in the animal. Direct incorporation of P65 DNA sequences into host cells may also be used to introduce the sequences into animal cells for expression of antigen in vivo.

The present invention also provides a method for testing a non-human animal, e.g., swine, bovine, etc., to determine whether the animal has been vaccinated with the vaccine of the present invention, other vaccines containing P65 protein, or is infected with naturally-occurring *Mycoplasma hyopneumoniae*. This method comprises obtaining from the animal a sample of suitable body fluid or tissue, detecting in the sample a presence of antibodies or other immune responses to *Mycoplasma hyopneumoniae* by reaction with a protein having an amino acid sequence depicted in FIG. 2 (SEQ ID NO:2), a fragment of said sequence capable of eliciting an antibody or other immune response which recognizes an epitope(s) of the amino acid sequence depicted in FIG. 2 (SEQ ID NO:2) or a mutant of said sequence capable of eliciting an antibody or other immune response which recognizes an epitope(s) of the amino acid sequence depicted in FIG. 2 (SEQ ID NO:2), the absence of such antibodies or other immune responses indicating that the animal has been neither vaccinated nor infected.

Alternatively, the fluid sample may be tested for the presence of a gene for *Mycoplasma hyopneumoniae* P65 by reaction with a recombinant or synthetic DNA sequence contained within the sequence shown in FIG. 1 (SEQ ID NO:1) or any RNA sequence, in RNA form, equivalent to said DNA sequence contained within the sequence shown in FIG. 1 (SEQ ID NO:1), the absence of said gene indicating that the animal has been neither vaccinated nor infected. Said test involving methods of synthesis, amplification or hybridization of nucleic acid sequences known within the scope of those skilled in the art.

EXAMPLES

Identification, Characterization and Modification of the *Mycoplasma Hyopneumoniae* P65 Structural Gene To isolate, clone and sequence the structural gene for the P65 lipoprotein from *M. hyopneumoniae*, a polyclonal antiserum to P65 was used to screen a recombinant phage library after infection of *E. coli* cells for the expression of any peptide epitope related to the *M. hyopneumoniae* P65 lipoprotein. The entire corresponding P65 gene was then isolated from overlapping chromosomal DNA fragments and characterized in detail, including its nucleotide sequence and its expression capability in *E. coli*. To manipulate the nucleotide sequence of this gene so that protein products related to P65 could be generated using universal expression systems in a heterologous host like *E. coli*, the DNA sequence was modified to standard codon usage, providing a foundation for overproduction and purification schemes described in the following section.

Figure 4:
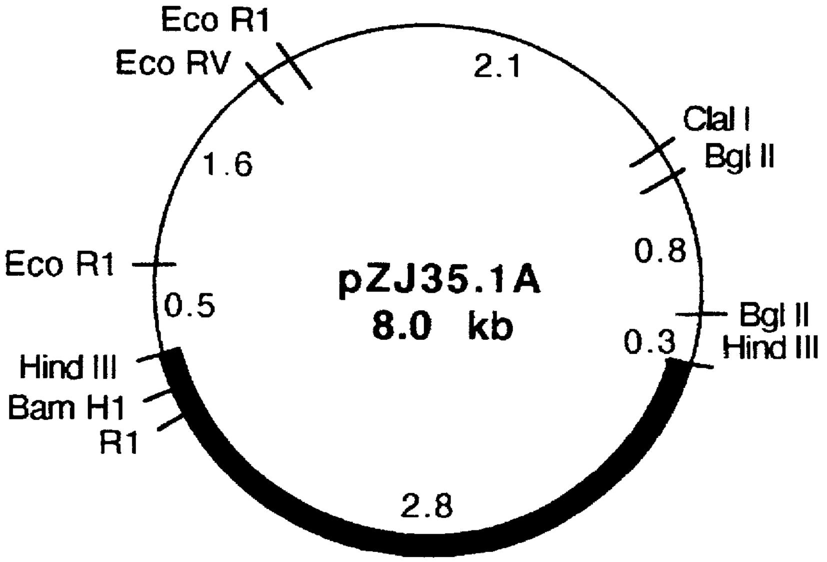
FIG. 4 is a diagram of plasmid pZJ35.1A. The region shown as an open box represents the 2672-bp fragment for which the entire nucleotide sequence is given in FIG. 1 (SEQ ID NO:1) and contains the complete P65 structural gene.

A recombinant phage from a *M. hyopneumoniae* genomic library was identified with antibodies to P65 and shown to produce a 19-kDa product (P19) that contained epitopes related to the authentic P65 lipoprotein (Kim et al., 1990, supra). DNA fragments from this phage were subcloned into the plasmid vector, pGEM3Z (Promega, Madison, Wis.) and one clone, pZJ25.1A (FIG. 3), which contained a 5.4-kb EcoRI fragment, was shown to express the P19 product. The sequence responsible for the expression of this 19-kDa C-terminal region of P65 was localized to an 800-bp region at one end of this fragment (shown in FIG. 3), but the remainder of the P65 gene was not contained in these sequences. An overlapping 5.0-kb HindIII fragment was isolated as the recombinant plasmid pZJ35.1A (FIG. 4) and shown to contain the entire P65 structural gene. This plasmid also expressed the P19 product and a P40 polypeptide, both containing epitopes related to P65 , but it did not express the full-length protein.

Figure 5:
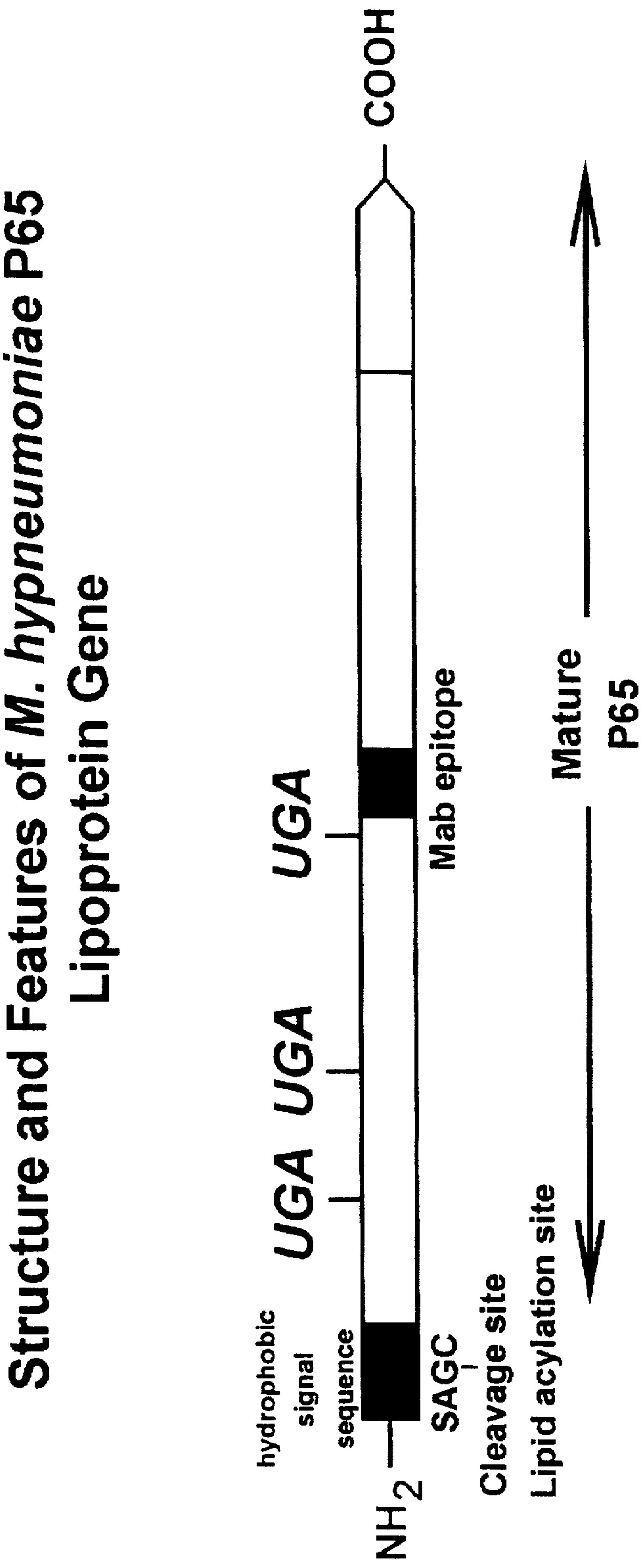
FIG. 5 is a schematic showing the structure and features of *Mycoplasma hyopneumoniae* P65 lipoprotein gene.

Nucleotide sequence was determined for a 2672-bp region of pZJ35.1A (the region noted in FIG. 4 and the sequence detailed in FIG. 1) (SEQ ID NO:1). The sequence encoded a 627-residue polypeptide (from nt313 to nt2193) which contained three internal, in-frame UGA codons (beginning at nt634, nt865, and nt1237) that designate tryptophan incorporation in mycoplasma proteins. These codons would prevent expression of the full-length P65 protein in *E. coli*. Downstream of these codons, positions for the internal initiation of translation leading to the synthesis of the P40 and P19 products were defined. The P65 coding region is shown schematically in FIG. 5. The 627-residue protein has a calculated molecular weight of 71,026, with a 29-amino acid hydrophobic signal sequence responsible for translocating the protein to the mycoplasma cell surface. The signal domain is bounded on its downstream end by the amino acid sequence SAGC which represents a typical lipoprotein processing site, leaving the C-residue modified (by fatty acid acylation) as the N-terminus of the mature protein. The calculated molecular weight of the mature protein, without modification, is 67,817.

In order to take advantage of the high-level *E. coli* expression systems to produce the full-length P65 product, the three in-frame UGA codons had to be changed to the universal tryptophan codon, UGG. The 1.3-kb EcoRI fragment containing all three UGA codons was removed from pZJ35.1A and cloned into the modified genome of the filamentous phage M13mp18 for oligonucleotide-directed mutagenesis. Oligonucleotides incorporating the UGA to UGG codon changes were generated for each of the three P65 gene regions, and standard reaction protocols were used to incorporate these changes into the P65 coding sequence. The mutagenized 1.3-kb EcoRI fragment was then removed from M13 and religated in place of the original fragment in pZJ35.1A to produce the mutated derivative pZJ35.1AM. This recombinant plasmid was shown to produce a P65 polypeptide in *E. coli* that contained the entire amino acid sequence of the mature mycoplasma protein and could be detected by polyclonal and monoclonal antibody (MAb) to P65.

Cloning and Overproduction of the Soluble Portion of P65 in an Expression Vector to Generate Two Forms of Recombinant P65.

Figure 6:
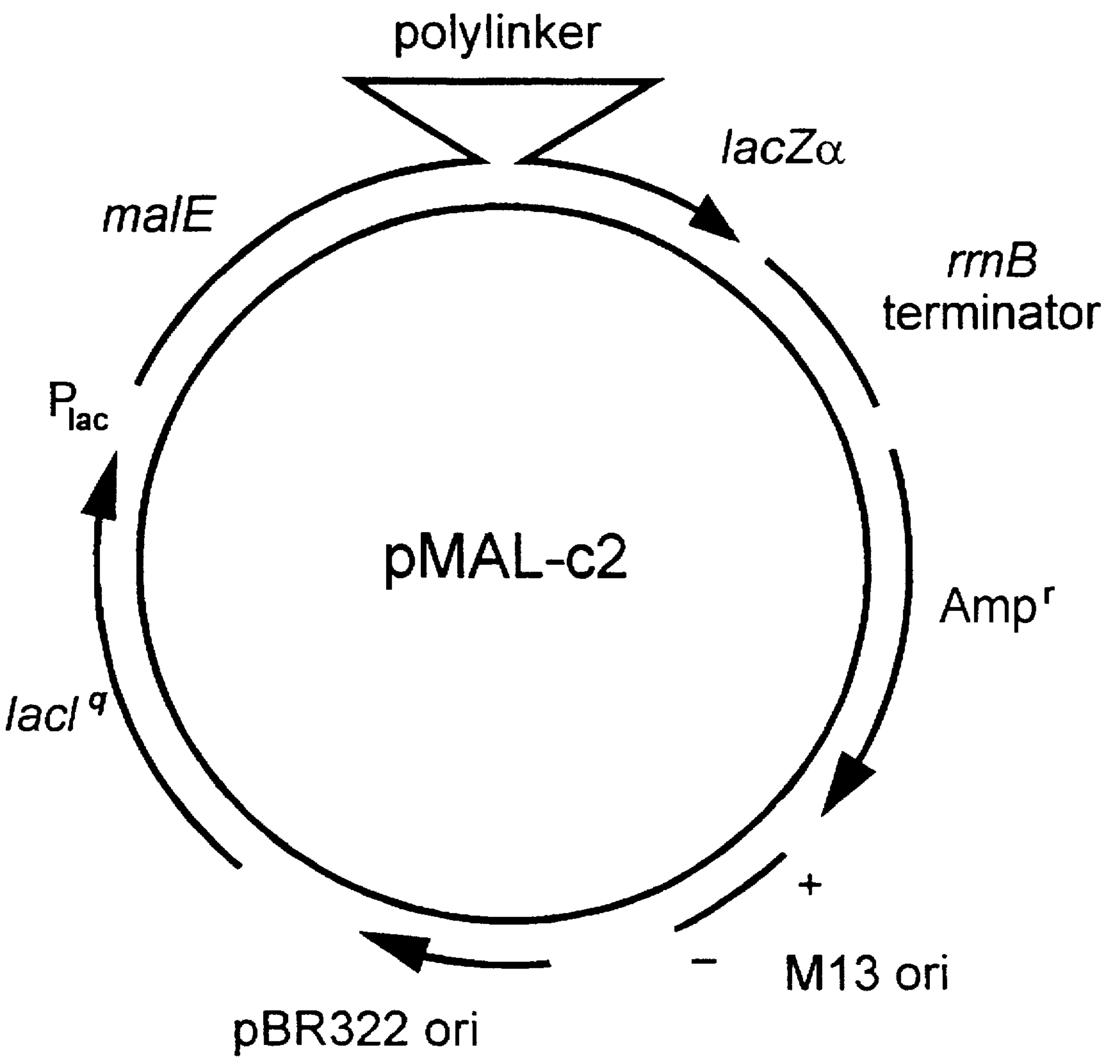
FIG. 6 is a diagram of expression of the vector pMAL-c2. The P65 structural gene was cloned into this vector as a BamHI-HindIII fragment ligated to the corresponding sites in the vector polylinker region.

To demonstrate that the full length P65 protein sequence could be expressed in a standard bacterial host with a conventional codon usage, and to show the feasibility of producing a soluble form of recombinant P65 that was abundant, easily purified and not denatured, a portion of the mutated P65 gene sequence was introduced into the expression vector pMAL-c2 (New England Biolabs, Beverly, Mass.)(NEB) shown in FIG. 6.

Figure 7:
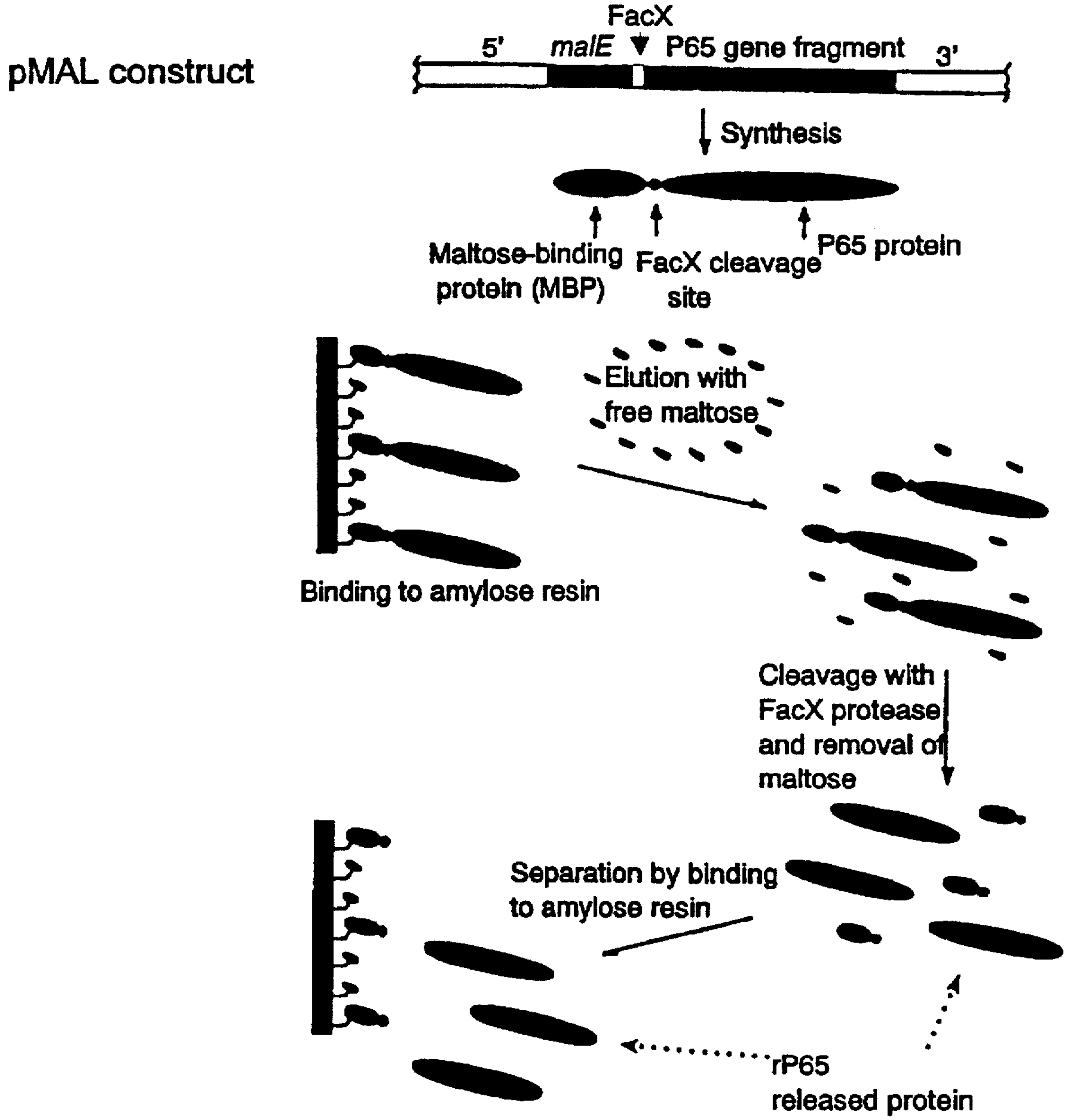
FIG. 7 is a schematic showing the purification of rP65.

The overall strategy created a gene fusion between part of the P65 coding sequence and the vector-borne malE gene (encoding maltose binding protein, or MBP, and under control of the inducible tac promoter), to create a fusion protein (FP65 ) which accumulated in the cytoplasm of the *E. coli* host as a soluble protein. Affinity chromatography using immobilized amylose then rendered a purified FP65 , which was assessed directly, or was cleaved with the specific protease, Factor Xa (at a site encoded at the 3' end of the malE gene in the original pMAL-c2), to liberate the P65 -containing portion of the fusion protein, from the MBP-containing portion (refer to FIG. 7).

To ensure a soluble product, yet to include all external, hydrophilic sequences of the authentic mycoplasmal P65 protein, a selected region of the P65 gene was used for this fusion in which the signal peptide sequence and lipid acylation site were eliminated. Specifically, the mutated sequence encoded in the construct pZJ35.1AM (FIG. 4) was subcloned, using the HindIII site 3' of the P65 coding region, but a 5' site created by polymerase chain reaction to include the UGU(Cys) codon at position 400, and a BamHI site 5' to that codon, designed to create an in-frame fusion by ligation with a BamHI site in the polylinker region of pMAL-c2. The polymerase chain reaction primer used to create the P65 gene fusion junction was: 5'-GGA TCC TCA GCT GGT TGT TTG C-3'.

Figure 8:
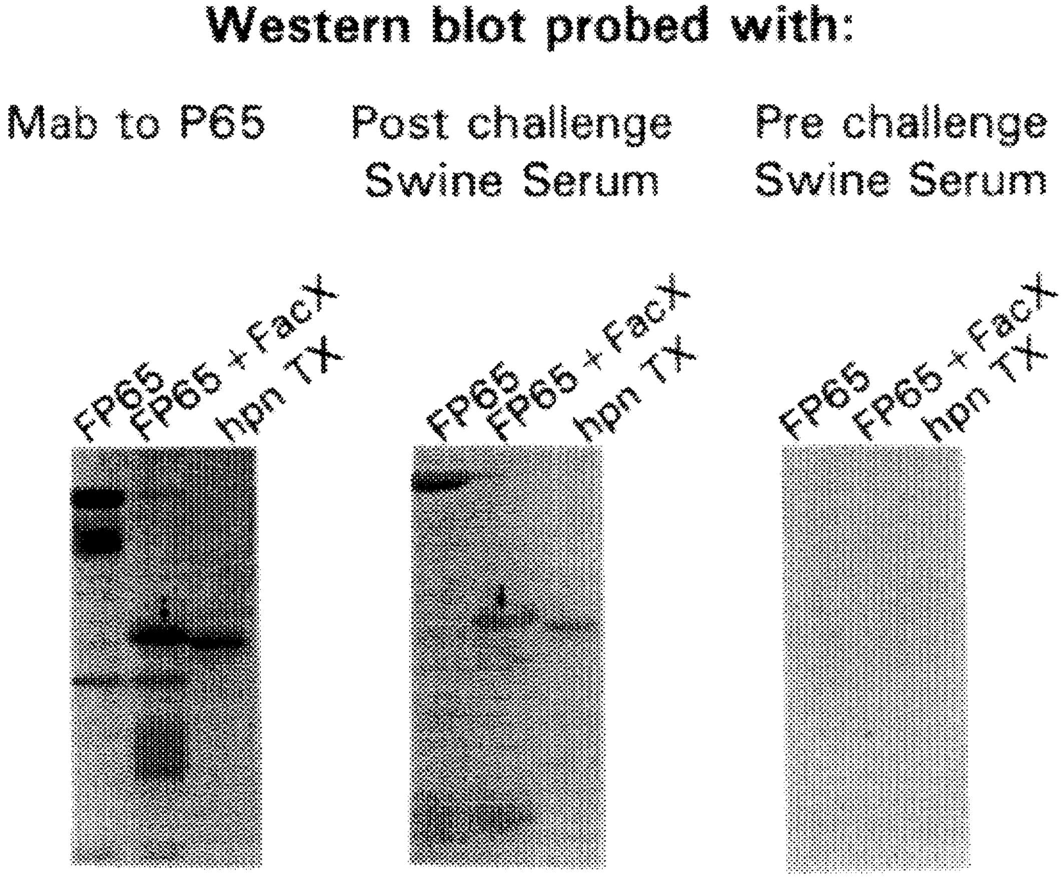
FIG. 8 shows the recognition of recombinant forms of P65 by the Mab defining this protein, and the selective recognition of the recombinant forms by swine infected with *Mycoplasma hyopneumoniae*. The three panels are Western blots of identical samples, immunostained with the Mab defining P65 (left panel), serum from swine after experimental inoculation with *Mycoplasma hyopneumoniae* (central panel), or serum from the same swine prior to inoculation (right panel). Antibodies and sera are described in Wise and Kim, 1990, supra; and Kim et al, 1990, supra. Each panel represents three preparations: affinity purified fusion protein FP65 (left lane of each panel), the same preparation treated with factor Xa to generate the rP65 fragment (arrows) (middle lane of each panel), or Triton X-114 phase membrane proteins of *Mycoplasma hyopneumoniae* (right lane of each panel). Minor bands in the left panel are breakdown products of the predominant FP65 or rP65 proteins, detected by sensitive Mab staining.

Demonstration of the Appropriate Recombinant Products, Recognition of Products by Antibodies of Swine Infected with *Mycoplasma Hyopneumoniae* and Solubility Properties Demonstration of the appropriate recombinant protein products is indicated in FIG. 8, showing the results of SDS-PAGE and Western blot analysis of the recombinant proteins (using methods described in Wise and Kim, 1987, supra; and Kim et al, 1990, supra). Induction of the recombinant pMAL-c2 construct in the cell line *E. coli* DH5 alpha (Life Technologies, Inc., Gaithersburg Md.) resulted in specific expression of a pronounced high molecular weight product observed in Coomasie blue stained SDS gels. This protein was purified by amylose column chromatography, by methods provided by the manufacturer of pMAL-c2 (NEB), and identified as the predicted FP65 by staining with the Mab to authentic P65 (FIG. 8, left panel). This protein was also identified with Mab to MBP (Chemicon International, Inc., Temecula, Calif.)(data not shown). In addition, the protein was cleaved with Factor Xa to generate the predicted product, rP65 , shown by the arrows in the middle lanes in the left and central panels in FIG. 8. (Staining of these factor Xa digests with Mab to MBP also showed the predicted MBP portion of the fusion protein, at approximately 43 kDa; data not shown). The liberated rP65 product was slightly larger than the authentic mycoplasmal P65 , as predicted from additional residues encoded by vector sequences that are absent from the processed form of the mature protein in mycoplasma. This is shown by staining the rP65 product and detergent phase proteins from the mycoplasma (hpn TX) with Mab to P65 (compare the middle and right lanes of the left panel in FIG. 8). In summary, the recombinant forms of P65 were authenticated by selective amylose binding and purification of the fusion protein FP65 , identification by MAbs recognizing P65 epitopes and MBP epitopes on the FP65 product, and selective cleavage of FP65 with factor Xa to liberate the expected rP65 product, also identified with the defining Mab to P65.

Recognition of the FP65 product and the factor Xa-liberated rP65 product by antibodies of swine infected with *M. hyopneumoniae* is demonstrated in FIG. 8, in the central and right panels, which are Western blots of the same samples represented in the left panel. Using swine serum from animals either prior to (prechallenge) or after (post challenge) experimental infection and disease caused by *M. hyopneumoniae* (described in Kim et al, 1990, supra), both the FP65 and the liberated rP65 protein were selectively recognized. (compare middle and right panels). Despite the use of the Western blot technique, which significantly denatures the proteins, the recombinant forms of P65 displayed epitopes that were selectively recognized by infected swine. The undenatured form of purified FP65 and rP65 show the same selective recognition by infected swine, in a standard enzyme-linked immunosorbent (ELISA) assay (data not shown).

Figure 9:
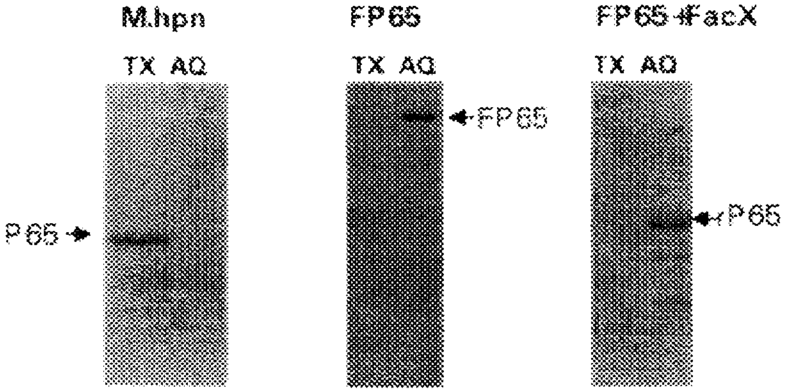
FIG. 9 shows the solubility properties of authentic and recombinant P65 after TX-114 fractionation by Western blot analysis.

The solubility properties of both FP65 and rP65 are shown in comparison to the authentic, lipid modified mycoplasma version, using detergent fractionation (Wise and Kim, 1987, supra and Kim et al 1990, supra). FIG. 9 shows that the FP65 and the liberated rP65 partition to the aqueous phase (Aq), whereas the native hydrophobic P65 migrates to the detergent phase (Tx). This insures that the recombinant products are soluble and easily manipulated in standard aqueous buffers.

In view of the above, it will be seen that the several objectives of the invention are achieved and other advantageous results attained. As various changes could be made in the above DNA molecules, proteins, etc. without departing from the scope of the invention, it is intended that all matter contained in the above description or shown in the accompanying drawings shall be interpreted as illustrative and not in a limiting sense.

What is claimed:

1. A vaccine for protecting a susceptible swine against mycoplasmal pneumonia caused by *Mycoplasma hyopneumoniae* comprising an immunogenic fusion protein in a suitable physiologically acceptable carrier, said fusion protein having a first amino acid sequence with the amino acid sequence depicted in FIG. 2 (SEQ ID NO:2), or immunogenic fragments thereof said first amino acid sequence being fused to a second amino acid sequence.

2. A method for inducing an immune response in a susceptible swine against mycoplasmal pneumonia caused by *Mycoplasma hyopneumoniae*, comprising administering to the swine a composition comprising an isolated and purified protein having the amino acid sequence depicted in FIG. 2 (SEQ ID NO:2), immunogenic fragments or immunogenic fusion proteins thereof in an amount effective for producing an immune response against mycoplasmal pneumonia caused by *Mycoplasma hyopneumoniae*.

3. A vaccine for protecting a susceptible swine against mycoplasmal pneumonia caused by *Mycoplasma hyopneumoniae* comprising an immunogenic fusion protein in a suitable physiologically acceptable carrier, said fusion protein having a first amino acid sequence encoded by the DNA in FIG. 1 (SEQ ID NO:1) said first amino acid sequence being fused to a second amino acid sequence.

* * * * *